United States Patent [19]

Elmaleh et al.

[11] Patent Number: 5,716,594
[45] Date of Patent: Feb. 10, 1998

[54] BIOTIN COMPOUNDS FOR TARGETTING TUMORS AND SITES OF INFECTION

[75] Inventors: David R. Elmaleh; Alan J. Fischman, both of Boston, Mass.; Timothy M. Shoup, De Catur, Ga.; John W. Babich, North Scituate, Mass.

[73] Assignee: The JMDE Trust, Newton, Mass.

[21] Appl. No.: 725,060

[22] Filed: Oct. 2, 1996

Related U.S. Application Data

[63] Continuation of Ser. No. 461,622, Jun. 5, 1995, abandoned, which is a continuation-in-part of Ser. No. 265,516, Jun. 24, 1994, abandoned, which is a continuation-in-part of Ser. No. 254,260, Jun. 6, 1994, abandoned.

[51] Int. Cl.$^6$ .................... A61K 51/00; A61K 35/00; A01N 43/50; C07D 235/02
[52] U.S. Cl. .................... 424/1.41; 424/1.73; 424/1.65; 424/9.36; 424/114; 534/14; 534/15; 514/387; 514/45; 548/302.7; 548/304.1; 548/303.7
[58] Field of Search .................... 424/1.41, 1.65, 424/1.11, 114, 1.69, 1.73, 9.3, 9.34, 9.36, 9.4; 548/302.7, 304.1, 303.7; 514/387, 45; 534/10, 14, 15, 16; 530/362, 367, 300

[56] References Cited

U.S. PATENT DOCUMENTS

| | | | |
|---|---|---|---|
| 4,863,713 | 9/1989 | Goodwin et al. | 424/1.1 |
| 5,135,736 | 8/1992 | Anderson et al. | 424/1.11 |
| 5,219,764 | 6/1993 | Huber et al. | 436/536 |
| 5,283,342 | 2/1994 | Gustavson et al. | 548/304.1 |
| 5,476,644 | 12/1995 | Illig et al. | 421/1.11 |

FOREIGN PATENT DOCUMENTS

| | | |
|---|---|---|
| WO 90/12096 | 10/1990 | WIPO. |
| WO 93/17714 | 9/1993 | WIPO. |
| WO 93/25240 | 12/1993 | WIPO. |
| WO 95/14493 | 6/1995 | WIPO. |

OTHER PUBLICATIONS

Garlick, R.K. and R.W. Giese, "Avidin Binding of Radiolabeled Biotin Derivatives", *J. Biological Chemistry*, vol. 263, No. 1, pp. 210-215 (5 Jan. 1988);.

Hnatowich, D.J., et al., "Investigations of Avidin and Biotin for Imaging Applications", *J. Nuclear Medicine*, vol. 28, No. 8, pp. 1294-1302 (Aug. 1987);.

Hoffman, K. and Y. Kiso, "An approach to the targeted attachment of peptides and proteins to solid supports" *Proc. Natl. Acad. Sci. USA*, vol. 73, No. 10, pp. 3516-3518 (Oct. 1976);.

International Search Report for PCT/US95/07184 issued 13 Oct. 1995;.

Kalofonos, H.P., et al., "Imaging of Tumor in Patients with Indium-111-Labeled Biotin and Streptavidin-Conjugated Antibodies: Preliminary Communication" *Journal of Nuclear Medicine*, vol. 31, No. 11, pp. 1791-1796, (Nov. 1990);.

Koch, P. and H.R. Mäcke, "$^{99m}$Tc Labeled Biotin Conjugate in a Tumor 'Pretargeting' Approach with Monoclonal Antibodies" *Angewandte Chemie. Internatl. Ed.*, vol. 31, No. 11., pp. 1507-1509 (1 Nov. 1992);.

Shoup, T.M., et al. "The Evaluation of F-18 Labelled Biotin Derivatives for Tumor Localization with PET" *J. Nuclear Medicine*, vol. 33, No. 5, p. 1026, Abstract No. 853 (May 1992);.

Shoup, T.M., et al., "Synthesis and Evaluation of $^{18}$F-Labelled Biotin Derivatives for Tumor Localization with Pet" *IXth International Symposium on Radiopharmaceutical Chemistry*, Paris, 6-10 Apr. 1992;.

Shoup, T.M., et al., "Synthesis of Flourine-18-Labeled Biotin Derivatives: Biodistribution and Infection Localization" *J. Nuclear Medicine*, vol. 35, No. 10, pp. 1685-1690 (1994);.

Zhang, Z., et al. "Preparation of phototobin-DNA probes and their use for detection of *Plasmodium falciparum* DNA" *Chemical Abstracts*, vol. 113, No. 15, Abstract No. 128783 (8 Oct. 1990).

*Primary Examiner*—Gary E. Hollinden
*Assistant Examiner*—Michael G. Hartley
*Attorney, Agent, or Firm*—Fish & Richardson P.C.

[57] ABSTRACT

Novel biotin amide analogs that are useful for targeting therapeutic and imaging agents to sites of infection and tumors in vivo are disclosed.

24 Claims, No Drawings

BIOTIN COMPOUNDS FOR TARGETTING TUMORS AND SITES OF INFECTION

RELATED APPLICATIONS

This application is a continuation of application Ser. No. 08/461,622 filed on Jun. 5, 1995, now abandoned, Entitled: BIOTIN COMPOUNDS FOR TARGETTING TUMORS AND SITES OF INFECTION, which is a continuation in part of U.S. patent application Ser. No. 08/265,516, filed on Jun. 24, 1994, now abandoned, which itself is a continuation in part of U.S. patent application Ser. No. 08/254,260 filed on Jun. 6, 1994, now abandoned.

GOVERNMENT SUPPORT

Work described herein was support in part by funding from the Department of Energy under DOE grant DE-FG02-86ER60460.

BACKGROUND OF THE INVENTION

High contrast imaging of tumors can be achieved by allowing a nonradiolabeled antibody to localize and clear from the circulation prior to administration of a low molecular weight, radiolabeled moiety with high affinity for the pretargeted antibody (Paganelli, G. et al., *J. Nucl. Med Comm.* 12:211–234 (1991); Green, NM *Biochem. J.* 89:585–91 (1963); Hnatowich DJ et al., *J. Nucl. Med.* 28:1294–1302 (1987)). One such method utilizes the high affinity of avidin, a cationic glycoprotein found in egg whites, for biotin, a naturally occuring vitamin. Avidin is capable of binding four biotin molecules and forming an avidin-biotin complex with a very high affinity. ($Kd=10^{-15}M$).

Two basic approaches for targeting tumors with avidin-biotin systems have been used in patients and animals. In the first method, avidin (or streptavidin)-conjugated antibodies are injected and days later, when antibody-tumor binding is maximized, a radioactive biotin derivative is injected to localize the tumor. Unfortunately, incomplete clearance of unbound antibody from the blood circulation can obscure visualization of the target site. In the second method, blood background is reduced by injecting biotinylated antibodies followed three days later by cold avidin. The resultant circulating biotinylated antibody-avidin complexes are sequestered from the blood by the liver. Radioactive biotin is then injected and binds to the antibody-biotin-avidin complexes already localized in the tumor. However, by employing "pretargetting" steps, both approaches for targeting tumors require that a subject be available to undergo multiple procedures over the course of a few days.

A study by Morrel et al., reported uptake of In-111 labeled IgG and human serum albumin (HSA) in an *E. coli* infected rat model. The accumulation of both labeled proteins was found to be sufficient to produce clear images of the infection site (Morrel, EM et al., *J. Nucl. Med.* 30:1538–1545 (1989).

Simple, rapid methods for more specifically targeting therapeutic or imaging agents to tumors and sites of infection in vivo are needed.

SUMMARY OF THE INVENTION

In one aspect, the instant invention features biotin compounds that have a high specificity for target sites when administered to a subject in vivo. Preferred biotin compounds are biotin amide analogs and preferred target sites include tumors and sites of bacterial, vital or fungal infection. Particularly preferred biotin compounds show a target to non-target ratio of at least 5:1, are stable in vivo and substantially localize to target within 1 hour after administration. An especially preferred biotin amide analog is [3aS-(3aα, 4β, 6aα)]-hexahydro-2-oxo-1H-thieno [3,4d]imidazole-4-(N-3-(1-fluoropropyl))pentanamide.

In another aspect, the invention features pharmaceutical compositions comprised of a biotin compound. Preferred pharmaceutical compositions are biotin amide analogs having a therapeutic agent in the $R_6$ position. In a further aspect, the invention features new uses for the biotin compounds in treating or preventing the establishment or growth of tumors or sites of infection (e.g by pathogenic bacteria, viruses or fungi).

In a further aspect, the instant invention features biotin compounds further comprising an imaging agent and uses for the compounds in detecting and/or monitoring tumors or sites of infection in a subject. In one embodiment, the biotin compound imaging agent is administered in vivo and monitored using a means appropriate for the label. Preferred methods for detecting and/or monitoring a biotin compound imaging agent in vivo include Positron Emission Tomography (PET), and Single Photon Emission Computer Tomography (SPECT) and Magnetic Resonance Imaging (MRI).

The instant biotin compounds and in vivo methods for targetting therapeutic or imaging agents to a minor or site of infection do not require an initial pretargetting step. In addition, localization times are generally under 1 hour. Therefore, therapy or imaging can be accomplished in one short procedure. In addition, biotin compounds, which are natural small molecules that are rapidly cleared in vivo, are unlikely to have toxic side effects at the levels required for therapy or imaging.

Additional features and advantages of the invention will become more apparent from the following detailed description and claims.

DETAILED DESCRIPTION OF THE INVENTION

As used herein, the following terms and phrases shall have the meanings set forth below.

"Biotin compound" shall mean "biotin" (hexahydro-2-oxo-1H-thieno[3,4-d]imidazoline-4-valeric acid); a 244 dalton vitamin, conjugated to an imaging agent or therapeutic agent; or a "biotin amide analog", which is a compound having either of the following two structural formulas:

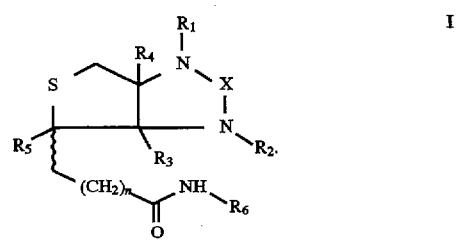

wherein, n=2–10;

$R_1$–$R_5$=H, acyl, alkyl, alkylene, alkenylene, alkynylene, alkenyl or alkynyl groups;

$R_6$=H, acyl, alkyl, alkylene, alkenylene, alkynylene, alkenyl or alkynyl groups; or a conjugated therapeutic agent or imaging agent; and X=C=O, S=O or C=NH—.
and

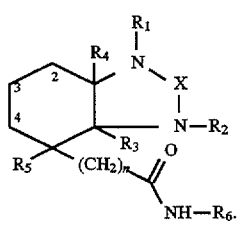

wherein, n=2–10;

$R_1$–$R_5$=H, acyl, alkyl, alkylene, alkenylene, alkynylene, alkenyl and alkynyl groups;

$R_6$=H, acyl, alkyl, alkylene, alkenylene, alkynylene, alkenyl and alkynyl groups; or a conjugated therapeutic agent or imaging agent X=C=O, S=O or C=NH; and positions 2, 3, or 4=O, S, or N The biotin amide analogs include racemic compounds and all possible enantiomers. The alkylene, alkenylene, alkynylene, alkenyl and alkynyl groups (hereinafter hydrocarbon groups) comprising the R groups can be either straight or branched chains, saturated or unsaturated. Unsaturated groups may have a single site of unsaturation or a plurality of unsaturated sites. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkyl or alkylene groups may be substituted with one or more oxygen or halogen atom to form alkoxy, haloalkyl, alkoxyene, and haloalkylene groups. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, astatine and iodine. Examples of substituted hydrocarbon groups which are useful within this invention are similar to hydrocarbon groups set forth above except for the incorporation of oxygen(s) or halogen(s) into the groups. Substitutions, which result in more lipophilic biotin compounds are preferred for targetting of tumors and sites of infection in the brain and spinal cord.

Especially preferred biotin compounds exhibit a high target to non-target ratio when administered in vivo. Preferably the ratio is $\geq 5:1$. A biotin compound can be glycosylated with a sugar moiety (e.g. glucose, fucose, galactose, mannose) that is recognized by a target specific receptor to further increase the target specificity of a compound. For example, biotin compounds can be glycosylated with mannose residues (e.g. attached as C-glycosides to a free nitrogen) to yield biotin compounds having higher affinity binding to tumors expressing mannose receptors (e.g. glioblastomas and gangliocytomas); and bacteria, which are also known to express mannose receptors (Bertozzi, CR and MD Bednarski *Carbohydrate Research* 223:243 (1992); *J. Am. Chem. Soc.* 114:2242,5543 (1992)) as well as potentially other infectious agents.

"conjugated" shall mean ionically or covalently attached (e.g. via a crosslinking agent).

An "imaging agent" shall mean a composition capable of generating a detectable image upon binding with a target and shall include radionuclides (e.g.In-111, Tc-99m, I-123, I-125 F-18, Ga-67, Ga-68, and for Positron Emission Tomography (PET) and Single Photon Emission Tomography (SPECT), unpair spin atoms and free radicals (e.g. Fe, lanthides and Gd) and contrast agents (e.g. chelated (DTPA) manganese) for Magnetic Resonance Imaging (MRI).

A "therapeutic agent" shall mean an agent capable of having a biological effect on a host. Preferred therapeutic agents are capable of preventing the establishment or growth (systemic or local) of a tumor or infection. Examples include drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense oligonucleotides that bind to a target nucleic acid sequence (e.g. mRNA sequence)), chemotherapeutic nucleotides, peptides, non-specific (non-antibody) proteins (e.g. sugar oligomers), boron containing compound (e.g. carborane), photodynamic agents (e.g. rhodamine 123), enediynes (e.g. calicheamicins, esperamicins, dynemicin, neocarzinostatin chromophore, and kedarcidin chromophore) and transcription based pharmaceuticals. In a preferred embodiment for treating or preventing the establishment or growth of a tumor, the therapeutic agent is a radionuclide, toxin, hormone antagonist, heavy metal complex, oligonucleotide, chemotherapeutic nucleotide, peptide, non-specific (non-antibody) protein, a boron compound or an enediyne. In a preferred embodiment for treating or preventing the establishment or growth of a bacterial infection, the therapeutic agent is an antibiotic, radionuclide or oligonucleotide. In a preferred embodiment for treating or preventing the establishment or growth of a viral infection, the therapeutic agent is an antiviral compound, radionuclide or oligonucleotide. In a preferred embodiment for treating or preventing the establishment or growth of a fungal infection, the therapeutic agent is an antifungal compound radionuclide or oligonucleotide.

A "target" shall mean an in vivo site to which biotin compounds bind. A preferred target is a tumor (e.g., tumors of the brain, lung (small cell and non-small cell), ovary, prostate, breast and colon as well as other carcinomas and sarcomas). Another preferred target is a site of infection (e.g. by bacteria, viruses (e.g. HIV, herpes, hepatitis) and pathogenic fungi (Candida sp.). Particularly preferred target infectious organisms are those that are drug resistant (e.g. Enterobacteriaceae, Enterococcus, *Haemophilus influenza, Mycobacterium tuberculosis*, Neisseria, *gonorrhoeae, Plasmodium falciparum, Pseudomonas aeruginosa, Shigella dysenteriae, Staphylococcus aureus, Streptococcus pneumoniae*). The localization of biotin at a site of infection, may be related to that fact that it is an essential nutrient of many bacteria, viruses and fungi.

"Subject" shall mean a human or animal (e.g. rat, mouse, cow, pig, horse, sheep, monkey, cat, dog, goat etc)

Method for Making Biotin Compounds

A variety of coupling or crosslinking agents such as protein A, carboiimide, dimaleimide, dithio-bis-nitrobenzoic acid (DTNB), N-succinimidyl-S-acetyl-thioacetate (SATA), and N-succinimidyl-3-(2-pyridyldithio) propionate (SPDP), 6-hydrazinonicotimide (HYNIC), $N_3S$ and $N_2S_2$ can be used in well-known procedures to synthesize biotin amide analogs or biotin compounds. For example, biotin can be conjugated via DTPA using the bicyclic anhydride method of Hnatowich et al *Int. J. Appl. Radiat. Isotop.* 33:327 (1982).

In addition sulfosuccinimidyl 6-(biotinamido) hexanoate (NHS-LC-biotin (which can be purchased from Pierce Chemical Co. Rockford, Ill.), "biocytin", a lysine conjugate of biotin, can be useful for making biotin compounds due to the availability of a primary amine. In addition, corresponding biotin acid chloride or acid precursors can be coupled with an aminoderivative of the therapeutic agent by known methods (See e.g. methods described in Examples 1 and 2).

Synthesized biotin compounds and biotin amide analogs can be characterized using standard methods of high field NMR spectra as well as IR, MS and optical rotation. Elemental analysis, TLC and/or HPLC can be used as a measure of purity. A purity of >98% is preferred. TLC and/or HPLC can also be used to characterize more lipophilic compounds.

Once prepared, candidate biotin derivatives can be screened for ability to bind avidin e.g. as described in the attached Example 3); for in vivo binding to sites of infection (e.g. as described in Example 4) or in vitro or in vivo binding to tumors. In addition, stability can be tested by administering the compound to a subject, obtaining blood samples at various time periods (e.g. 30 min, 1 hour, 24 hours) and analyzing the blood samples for the biotin compound and/or metabolites.

Two $^{18}$F biotin derivatives: an amide containing derivative (biotin 1) and an alkyl containing derivative (biotin 2) were prepared as described in Examples 1 and 2. Biotin 1 was easily synthesized from the sulfonate ester in good yield with high specific activity. Biotin 1 retains the basic structure of biotin. Biotin 2 was prepared to elucidate the role of the side chain on biotin binding to avidin and infection sites.

The two biotin derivatives were evaluated for binding to avidin in the presence of varying concentrations of unlabeled d-biotin as described in Example 3. Biotin 1 was found to bind to avidin and could be displaced by cold d-biotin. A scatchard transformation displacement curve yielded a Kd of $3.12\times10^{-14}$M with a Bmax of $5.57\times10^{-16}$M. In contrast, compound 2 showed no specific binding to avidin.

Both compounds were then evaluated for localization at sites of infection in *E. coli* infected rats as described in Example 4. Half of the infected rats were treated with avidin 24 hours prior to i.v. injection of the $^{18}$F-labeled biotin analogs. Biotin 1, without avidin pretreatment, showed a high selectivity (6.08±1.12) for infected compared to normal muscle at 60 minutes post injection. This ratio increased only slightly by administration of avidin 24 hr prior to injection of $^{18}$F-labeled biotin 1 (6.39±0.96).

In contrast, the biodistribution of biotin 2 indicated more binding to normal muscle with an infection/normal muscle ratio of 0.58±0.07. This lack of selectivity illustrates the importance of the side-chain amide group in infection localization. Some defluorination of both biotin 1 and biotin 2 occured in vivo as evidenced by increased $^{18}$F bone uptake after 60 min.: 2.94±0.37 and 1.17±0.21%IG/g±s.d.; respectively.

Use of Biotin Compounds as Therapeutics

For use in therapy, an effective amount of an appropriate biotin compound can be administered to a subject by any mode, which allows the compound to be taken up by the appropriate target. Preferred routes of administration include oral and transdermal (e.g. via a patch). Examples of other routes of administration include injection (subcutaneous, intravenous, parenteral, intraperitoneal, intrathecal, etc.). The injection can be in a bolus or a continuous infusion. Depending on the route of administration, the biotin compound, therapeutic agent can be coated with or disposed in a selected material (e.g. positively or negatively charged liposomes), to protect it from natural conditions which may detrimentally effect its ability to perform its intended function, increase its in vivo availability or increase its uptake by a specific organ.

A biotin compound therapeutic agent can be administered alone, or in conjunction with a pharmaceutically acceptable carrier. As used herein, the phrase "pharmaceutically acceptable carrier" is intended to include substances that can be coadministered with a biotin compound therapeutic agent and allows the compound to perform its intended function. Examples of such carriers include solutions, solvents, dispersion media, delay agents, emulsions and the like. The use of such media for pharmaceutically active substances are well known in the art. Any other conventional carrier suitable for use with the biotin compounds also falls within the scope of the present invention.

The language "effective amount" of a biotin compound therapeutic agent refers to that amount necessary or sufficient to eliminate, reduce or maintain (e.g prevent the spread of) an infection, tumor or other target. The effective amount can vary depending on such factors as the disease or condition being treated, the particular biotin compound being administered, the size of the subject, or the severity of the disease or condition. One of ordinary skill in the art can empirically determine the effective amount of a particular compound without necessitating undue experimentation.

A preferred dose for treating or preventing a tumor or site of infection is in the range of 5 μg–100 mg. However, the exact dose depends to a great extent on the toxicity of the therapeutic agent being administered. For example, a subject can not withstand more than a milligram dose of bleomycin. In addition, certain chemotherapeutic peptides cause hemophilia and other blood disorders when given to a subject in microgram amounts. However, the selective targeting of a therapeutic agent by the instant biotin compounds decreases their otherwise toxic effects on normal body cells.

Use of Biotin Compounds as Imaging Agents

Biotin compounds can be labeled with a variety of imaging agents, which are known in the art and which will depend to some extent on the means used to detect or monitor the compound in vivo or in vitro. Preferred imaging agents for performing positron emission tomography (PET), and single photon emission computer tomography (SPECT) include F-18, Tc-99m, and I-123. Preferred imaging agents for magnetic resonance imaging (MRI) include an appropriate atom with unpaired spin electrons or a free radical. An imaging agent can be complexed with a biotin compound by a variety of techniques that are well-known in the art. In a preferred embodiment, the imaging agent is attached via the amine to a HYNIC, DTPA or other chelating agent.

Biotin compounds that have been labeled with an appropriate imaging agent can be added to a particular tumor cell line or bacterial, viral or fungal infected tissue culture to test the binding affinity of a particular candidate biotin compound therapeutic.

Labeled biotin compounds can also be injected into an appropriate subject (e.g. monkey, dog, pig, cow) and its binding with tumors or sites of infection in vivo (e.g. as described in the following Example 4).

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Synthesis of Two $F^{18}$-Labeled Biotin Analogs

Analysis for carbon and hydrogen was performed by Galbraith Laboratories (Knoxville, Tenn.). Melting points were measured with a Fisher-Johns apparatus and are uncorrected. Proton NMR spectra ($d_6$-DMSO) were acquired with a Bruker AM 500 instrument; the chemical shifts are reported in parts per million (delta) down field from tetramethylsilane. All reagents were purchased from Aldrich Chemical Co., (Milwaukee, Wis.) and were used without further purification. Acetonitrile ws purchased from Pierce (Rockford, Ill.) and used as shipped.

Thin layer chromatography was performed on silica gel Gf 250 plates (Analtech, Inc., Newark, Del.). Chromatograms of the radiolabeled compounds were counted with a Bioscan System 200 (Washington, D.C.). High pressure liquid chromatography was performed on a Resolvex C18 column (4.6 mm×25 cm, Fisher Scientific Co.) at a flow rate of 1 ml/min using water/acetonitrile (60:40) solvent system. Separation was monitored with a U.V. detector ($\lambda$=185 nm) and a NaI (T1) radioactivity detector.

Synthesis of [3aS-(3a$\alpha$, 4$\beta$, 6a$\alpha$)]-hexahydro-2-oxo-1H-thieno [3, 4d]imidazole-4-(N-3-(1-fluoropropyl))pentanamide (Biotin 1)

(+)Biotin (1 g, 4.09 mmol) was added to 20 ml of a stirred 50/50 mixture of thionyl chloride and benzene and the mixture was refluxed under $N_2$ for 2 h. Excess thionyl chloride was removed by distillation and the residue was cooled to room temperature under $N_2$, dissolved in dry THF (10 ml) and added to a stirred solution of 3-amino-1-propanol (1 g) in THF (20 ml) at 25° C. The solvent was removed by roto-evaporation, and excess amino propanol was removed at 120° C. under vacuum (1 torr). The crude material was purified by chromatography on a silica gel column (30 g) eluted with $CH_2Cl_2$/MeOH/$HCO_2$H (20:80:0.5). Crystallization from MeOH gave 0.80 g (65%) of product. This product showed a single spot ($R_f$=0.45) on TLC with $CH_2Cl_2$/MeOH/$HCO_2$H (20:80:0.5); mp=130°–132° C. $^1$H NMR ($d_6$-DMSO) d2.05 (t, J=6.2 Hz, 2H, $CH_2$—O), 3.2–3.5 (m, 6H, N—$CH_2$—), 6.35 (s, 1H, O=CNH-ring), 6.40 (s, 1H, O=CNH-ring), 7.75 (t, J=5.6 Hz, 1H, O=CNH). Anal. Calcd. for $C_{13}H_{23}N_3O_3S$: C, 51.80, H, 7.70. Found: C, 51.69; H, 7.51.

The product (100 mg, 0.33 mmol) was dissolved in 3 ml of dry pyridine by heating and stirring under $N_2$. The solution was cooled to room temperature, and 0.7 mL of a 0.87M solution of methansulfonyl chloride in $CH_2Cl_2$ was added. After 30 min., the mixture was chromatographed on silica gel using acetone/acetonitrile (90:10). The product (86 mg, 69%) showed a single spot on TLC ($R_f$=0.49) with MeOH/$CH_2Cl_2$/$HCO_2$H (10:90:0.5) that was visualaized with $MoO_3$.$H_3PO_4$.

A 10-ml reactivial containing KF (48 mg), Kryptofix (300 mg), biotin mesylate (200 mg), and 7 ml of acetonitrile was heated at 110° C. for 30 min. The solvent was roto-evaporated and the residue was chromatographed on silica gel (25 g) using $CH_2Cl_2$/MeOH/$HCO_2$H (85:15:0.5). This product, [3aS-(3a$\alpha$, 4$\beta$, 6a$\alpha$)]-hexahydro-2-oxo-1H-thieno[3,4d]imidazole-4-(N-3-(1-fluoropropyl))pentanamide (Biotin 1), showed a single spot ($R_f$=0.38) by TLC with the same solvent. $^1$H NMR ($d_6$-DMSO) d3.2–3.5 (m, 6H, N—$CH_2$—), 4.4 (dt, J=52, 6.5 Hz, 2H, $CH_2$—F), 6.35 (s, 1H, O=CNH-ring), 6.40 (s, 1H, O=CNH-ring), 7.75 (t, J=5.6 Hz, 1H, O=CNH). Anal. Calcd. for $C_{13}H_{22}N_3O_2SF$: C, 54.90, H, 7.80. Found: C, 52.19; H, 8.13.

Synthesis of [3aS-(3a$\alpha$, 4$\beta$, 6a$\alpha$)]-tetrahydro-4-(5-(1-[$^{18}$F]fluoro-pentyl)-1H-thieno[3,4-d]imidazol-2 (3H)-one (Biotin 2)

To a stirred suspension of lithium aluminum hydride (LAH) (1.0 g, 25.8 mmol) in anhydrous ether (125 ml), a hot pyridine (25 ml) solution of (+)biotin (1.0 g, 4.01 mmol) was added dropwise. After addition, the reaction mixture was stirred at room temperature for 30 min. and then heated to reflux for an additional 30 min. The excess LAH was then destroyed by careful dropwise addition of water. Water and organic solvents were removed by roto-evaporation. The residue was acidified (pH 2) with 6N HCl and the water was removed by roto-evaporation. The residue was extracted with chloroform (5×20 mL) and the choroform layer evaporated in vacuo to give a white solid. Recrystallization from methanol gave 0.44 g (50%) of the reduced product; mp 164°–167° C. (reference 11, mp 164°–169° C.). $^1$H NMR ($d_6$-DMSO) d 4.35 (t, J=6 Hz, 2H, O—$CH_2$—), 6:35 (s, 1H, O=CNH-ring), 6.40 (s, 1H, O=CNH-ring).

To a solution of (+)Biotinol (100 mg, 0.43 mmol) in pyridine (3 ml) was added 0.6 mL of a 0.87M solution of thionyl chloride in $CH_2Cl_2$. The mixture was stirred for 30 min. followed by chromatography on silica gel using acetone/acetonitrile 90:10. The product (96 mg, 75%) showed a single spot on TLC ($R_f$=0.42) with EtOAc/$CH_2Cl_2$/acetone/$HCO_2$H (10:80:10:0.5) that was visualized with $MoO_3$.$H_3PO_4$.

Biotin 2 was prepared from biotinol mesylate in the same manner as described for [3aS-(3a$\alpha$, 4$\beta$, 6a$\alpha$)]-hexahydro-2-oxo-1H-thieno[3,4d]imidazole 4-(N-3-(1-fluoropropyl)) pentanamide above. [3aS-(3a$\alpha$, 4$\beta$, 6a$\alpha$)]-tetrahydro-4-(5-(1-[$^{18}$F]fluoropentyl)-1H-thieno[3,4-d]imidazol-2(3H)-one was purified on silica gel using EtOAc/$CH_2Cl_2$/acetone/$HCO_2$H (10:80:10:0.5) (Rf=0.48); mp 110°–112° C. $^1$H NMR ($d_6$-DMSO) d 4.6 (dr, J=55, 6.5 Hz, F—$CH_2$—), 6.35 (s, 1H, O=CNH-ring), 6.40 (s, 1H, O=CNH—ring). Anal. Calcd. for $C_{10}H_{16}N_2OSF$: C, 56.31, H, 7.57. Found: C, 56.59; H, 7.79.

Preparation of $^{18}$F-Labeled Biotin 1 and Biotin 2

$^{18}$F-Labeled Biotin 1. [$^{18}$F] Fluoride was produced with a cyclotron by the $^{18}$O(p,n) $^{18}$F nuclear reaction on $^{18}$O-enriched water in a silver plated target at 17 MeV, 20 mA-.hr. (Scanditronix, Sweden, MC17F) (Kilbourn MR, Jerabek PA, Welch MJ. An improved [$^{18}$O]water target for [$^{18}$F]fluoride production. Int J Appl Radiat Isot 36:327–328 (1985).

A 5-ml reactivial containing $^{18}$F in $H_2^{18}$O (50 mCi, 1 mL), Kryptofix (3 mg), and $K_2CO_3$ (1 mg) ws evaporated to dryness at 100° C. under $N_2$. The contents were dried by addition of acetonitrile (4×2 mL) with heating at 110° C. under a stream of $N_2$. Biotin mesylate (2 mg) in acetonitrile (1 mL) was added and the vial was sealed and heated at 110° C. for 10 min. Solvent was removed and the labelled product purified by chromatography on a short column of silica gel (10 g) using MeOH/$CH_2Cl_2$/$HCO_2$H (20:80:0.5). The time required for synthesis and purification was 90 min. (from the end of bombardment) and the radiochemical yield was 3.4 to 5.9 mCi (12–21%, EOS). HPLC analysis of the final product showed a single radioactive peak with a retention time ($R_t$) 2.8 min. corresponding to that of the [$^{19}$F]fluoro-biotin. The chemical purity of [3aS-(3a$\alpha$, 4$\beta$, 6a$\alpha$)]-hexahydro-2-oxo-1H-thieno[3,4-d]imidazole-4-(nnN-3-(1-[$^{18}$F fluoropropyl)) pentanamide was >8%.

$^{18}$F-Labeled Biotin 2. $^{18}$F-labeled Biotin 2 was prepared in the same manner as $^{18}$F-labeled Biotin 1. $^{18}$F-labeled Biotin 2 was purified on silica gel (10 g) using EtOAc/$CH_2Cl_2$/acetone/$HCO_2$H (10:80:10:0.5). The radiochemical yield was 5.6 mCi (20%, EOS) and radiochemical purity was determined to be greater than 98%. The chemical purity of 3aS-(3a$\alpha$, 4$\beta$, 6a$\alpha$)]-tetrahydro-4-(5-(1-[$^{18}$F] fluoropentyl)-1H-thieno-[3,4-d]imidazol-2(3H)-one was >98% by HPLC.

EXAMPLE 2

Competitive Binding of F-18 Labeled Biotin 1 and Biotin 2 to Avidin vs. d-Biotin A preliminary measure of the binding characteristics of the fluoro analogs of biotin were performed. The binding of these novel F-18 labeled biotin analogs to avidin was evaluated by measuring the binding of F-18 labeled biotin analogs to avidin in the presence of varying concentrations of unlabeled d-biotin. Serial dilutions of d-biotin were prepared in phopshate buffered saline pH 7.4 (PBS). A fixed quantity of the no-carrier added F-18 labeled biotin 1 or 2 (10–100 µCi) were mixed with each d-biotin dilution so that the range of concentrations of cold biotin were 3 orders of magnitude greater and less than the concentration of avidin ($10^{-16}$M). A 200 µl aliquot of the F-18 biotin/cold biotin solution was added to 200 µl of avidin in PBS. The solution was vortexed and allowed to incubate for 1 hour after which time a 5 µl aliquot of the solution was analysed by instant thin layer chromatography (Gelman ILTC-SG) using 0.1M acetate buffer pH 6.0. In this chromatographic system the F-18 biotin analogs bound to avidin origin while the unbound F-18-biotin analogs move to the solvent front. Percent binding of F-18 biotin analog was calculated as [(counts at origin/total counts)*100]. For each F-18-biotin analog potential impurities remaining at the origin were determined and the results of binding corrected accordingly.

EXAMPLE 3

Biodistribution Studies in Rats

A clinical isolate of *E. Coli* was stored at −70° C. in a freezing media containing 20% glycerol and 80% dextrose phosphate until use. Aliquots of bacteria were defrosted and colony counts performed on serial dilutions grown overnight on BBL Brucella agar plates. Based on the colony count, fleshly thawed bacteria suspensions were washed and diluted with saline to a final concentration of $8 \times 10^{10}$ organisms/ml. Aliquots (0.1 ml) of bacterial suspensions ($8 \times 10^9$ organisms/ml) were injected into the right thigh muscle of 48 male Sprague-Dawley rats (125–150 g, Charles River Breeding Laboratories, Burlington, Md.). Twenty-four rats were used for each labeled biotin compound. Twenty-four hours after injection, swelling in the right thigh readily appeared, and 24 rats each received 1.67 mg of avidin in saline via the tail vein. Forty-eight hours after bacterial inoculations, 80 to 150 mCi of $^{18}$F-biotin 1 or 2 was administered. Rats were sacrificed at 5 and 60 min. post-injection, six rats per time point. Blood samples were obtained by cardiac puncture. Syringes were weighed before and after injection to determine the volume delivered. The activity per unit volume was obtained from standards. A total of eleven different tissues were excised, weighed, and counted. These tissues included blood; bone; lung; liver; adrenal; spleen; kidneys; heart; muscle (thigh); teste; and infected muscle (thigh). The excised tissues were blotted, weighed, and counted in a scintillation well counter. The raw counts were decay corrected. The results were expressed as percent injected dose per gram, and infection-to-normal muscle ratios (mean±s.d.). The biodistribution results were evaluated by analysis of variance (one-way ANOVA). The effect of avidin pretretment on biodistribution was evaluated by student t-test.

Table 1 shows the biodistribution of $^{18}$F-labeled biotin 1 at 5 and 60 min. after injection in rats with and without avidin pretreatment (24 hr). Analysis of variance demonstrated a significant main effects of organs (P<0.001) at 5 and 60 min. on biotin 1 accumulation. At 5 min. accumulation of 1 in kidney was greater than in all other organs (4.5-fold higher than blood) (P<0.001). Accumulation of 1 in liver and spleen were greater than normal muscle (P<0.02). Sufficient clearance of radioactivity had occurred within 60 min. in all other organs relative to infection except for bone (P<0.001). At 60 min., the selectivity for infected compared to normal muscle was 6.08±1.12 (Table 2); accumulation in infected muscle was greater than kidney (P<0.05), blood (P<0.01), spleen (P<0.01), liver (P<0.001), and normal muscle (P<0.001). The distribution of biotin 1 in all organs did not change significantly with avidin-pretreatment at 5 min. At 60 min. with pretreatment, accumulation in bone (P<0.01) was less than without avidin-pretreatment. Compared to untreated rats, accumulation of 1 in avidin-treated rats was greater in kidney (P<0.02), blood (P<0.05), and normal muscle (P<0.002).

TABLE 1

Tissue distribution of $^{18}$F-labeled biotin 1 in *E. coli* infected rats

| Tissue | Without Avidin 5 Min. | Without Avidin 60 Min. | With Avidin 5 Min. | With Avidin 60 Min. |
|---|---|---|---|---|
| Blood | 1.07 ± 0.31 | 0.14 ± 0.02 | 1.13 ± 0.11 | 0.19 ± 0.04 |
| Heart | 1.00 ± 0.34 | 0.14 ± 0.02 | 0.99 ± 0.12 | 0.09 ± 0.01 |
| Lung | 1.21 ± 0.13 | 0.11 ± 0.02 | 1.07 ± 0.21 | 0.13 ± 0.02 |
| Liver | 1.39 ± 0.16 | 0.13 ± 0.03 | 1.29 ± 0.17 | 0.16 ± 0.02 |
| Spleen | 1.40 ± 0.30 | 0.14 ± 0.03 | 1.52 ± 0.32 | 0.19 ± 0.0 |
| Kidney | 4.78 ± 0.80 | 0.23 ± 0.05 | 4.01 ± 0.77 | 0.32 ± 0.04 |
| Adrenal | 1.00 ± 0.20 | 0.09 ± 0.02 | 0.85 ± 0.13 | 0.11 ± 0.02 |
| Teste | 0.57 ± 0.02 | 0.16 ± 0.03 | 0.50 ± 0.11 | 0.19 ± 0.04 |
| Norm mus | 0.83 ± 0.09 | 0.078 ± 0.02 | 0.82 ± 0.12 | 0.10 ± 0.02 |
| Inf mus | 1.22 ± 0.36 | 0.43 ± 0.10 | 0.99 ± 0.11 | 0.65 ± 0.14 |
| Bone | 1.10 ± 0.16 | 2.94 ± 0.37 | 1.19 ± 0.23 | 2.29 ± 0.14 |

TABLE 2

Infected to normal tissue ratios of $^{18}$F-labeled biotin 1 in *E. coli* infected rats.

| Tissue | Without Avidin 5 Min. | Without Avidin 60 Min. | With Avidin 5 Min. | With Avidin 60 Min. |
|---|---|---|---|---|
| Blood | 1.30 ± 0.86 | 3.09 ± 0.54 | 0.90 ± 0.14 | 3.75 ± 0.75 |
| Heart | 1.21 ± 0.26 | 6.21 ± 0.57 | 1.08 ± 0.18 | 7.59 ± 1.34 |
| Lung | 1.00 ± 0.23 | 4.21 ± 0.69 | 1.06 ± 0.30 | 4.83 ± 0.91 |
| Liver | 0.89 ± 0.25 | 3.48 ± 0.67 | 0.83 ± 0.16 | 4.05 ± 0.65 |
| Spleen | 0.94 ± 0.49 | 2.98 ± 0.30 | 0.64 ± 0.11 | 3.34 ± 0.72 |
| Kidney | 0.26 ± 0.05 | 1.96 ± 0.24 | 0.28 ± 0.06 | 2.04 ± 0.35 |
| Adrenal | 1.06 ± 0.24 | 5.20 ± 1.20 | 1.20 ± 0.22 | 5.74 ± 1.14 |
| Teste | 2.14 ± 0.60 | 2.87 ± 0.50 | 2.00 ± 0.37 | 3.35 ± 0.56 |
| Norm mus | 1.54 ± 0.69 | 6.08 ± 1.12 | 1.24 ± 0.20 | 6.39 ± 0.96 |
| bone | 1.06 ± 0.33 | 0.16 ± 0.04 | 0.90 ± 0.18 | 0.28 ± 0.07 |

The biodistribution of biotin 2 in rat tissues is shown in Table 3. Five minutes after injection, without avidin, accumulation of biotin 2 in liver, kidney, and adrenal was greater than blood (P<0.001), heart (P<0.001), spleen (P<0.001), muscle (P<0.001), and bone (P<0.001). At 60 min. accumulation of biotin 2 in bone was greater than all other organs (P<0.001) and accumulation in adrenal and lung was greater than kidney (P<0.05), liver (P<0.02), normal muscle (P<0.001) and blood (P<0.001). The infected/normal tissue ratio was 0.58±0.07 indicating more binding to normal muscle than to the infection (Table 4). At 5 min. with avidin pretreatment, there was a decrease in accumulation of 2 in adrenal (P<0.01), kidney (P<0.001), spleen (P<0.001), and heart (P<0.05) compared to untreated rats. At 60 min. there was greater accumulation in blood (P<0.05), heart (P<0.05), spleen (P<0.001), kidney (P<0.01), and normal muscle (P<0.05) relative to untreated rats. Avidin pretreatment did not change the infected/normal tissue ratio.

TABLE 3

Tissue distribution of ¹⁸F-labeled biotin 2 in E. coli infected rats.

| Tissue | Without Avidin 5 Min. | 60 Min. | With Avidin 5 Min. | 60 Min. |
|---|---|---|---|---|
| Blood | 0.88 ± 0.07 | 0.30 ± 0.02 | 0.85 ± 0.04 | 0.25 ± 0.03 |
| Heart | 0.80 ± 0.06 | 0.25 ± 0.03 | 0.96 ± 0.10 | 0.20 ± 0.03 |
| Lung | 1.38 ± 0.21 | 0.58 ± 0.10 | 1.59 ± 0.16 | 0.55 ± 0.12 |
| Liver | 1.63 ± 0.27 | 0.42 ± 0.03 | 1.91 ± 0.22 | 0.55 ± 0.13 |
| Spleen | 1.70 ± 0.68 | 0.26 ± 0.01 | 0.99 ± 0.10 | 0.51 ± 0.09 |
| Kidney | 1.62 ± 0.18 | 0.57 ± 0.04 | 2.70 ± 0.48 | 1.39 ± 0.21 |
| Adrenal | 1.56 ± 0.14 | 0.92 ± 0.21 | 2.00 ± 0.24 | 0.72 ± 0.12 |
| Teste | 0.59 ± 0.08 | 0.20 ± 0.03 | 0.74 ± 0.11 | 0.15 ± 0.02 |
| Norm mus | 0.62 ± 0.09 | 0.35 ± 0.09 | 0.69 ± 0.10 | 0.28 ± 0.04 |
| Inf mus | 0.49 ± 0.05 | 0.20 ± 0.02 | 0.44 ± 0.05 | 0.18 ± 0.02 |
| bone | 0.73 ± 0.09 | 1.17 ± 0.21 | 0.86 ± 0.12 | 1.10 ± 0.20 |

TABLE 4

Infected to normal tissue ratios of ¹⁸F-labeled biotin 2 in E. coli infected rats.

| Tissue | Without Avidin 5 Min. | 60 Min. | With Avidin 5 Min. | 60 Min. |
|---|---|---|---|---|
| Blood | 0.56 ± 0.04 | 0.68 ± 0.06 | 0.51 ± 0.07 | 0.71 ± 0.05 |
| Heart | 0.61 ± 0.03 | 0.81 ± 0.05 | 0.46 ± 0.03 | 0.91 ± 0.05 |
| Lung | 0.36 ± 0.05 | 0.43 ± 0.20 | 0.28 ± 0.02 | 0.33 ± 0.06 |
| Liver | 0.31 ± 0.04 | 0.48 ± 0.33 | 0.23 ± 0.02 | 0.33 ± 0.05 |
| Spleen | 0.70 ± 0.04 | 0.78 ± 0.08 | 0.44 ± 0.05 | 0.35 ± 0.04 |
| Kidney | 0.30 ± 0.02 | 0.35 ± 0.03 | 0.16 ± 0.02 | 0.13 ± 0.02 |
| Adrenal | 0.31 ± 0.02 | 0.23 ± 0.05 | 0.22 ± 0.03 | 0.214 ± 0.03 |
| Teste | 0.84 ± 0.10 | 1.04 ± 0.11 | 0.59 ± 0.03 | 1.15 ± 0.06 |
| Norm mus | 0.80 ± 0.12 | 0.58 ± 0.07 | 0.65 ± 0.10 | 0.64 ± 0.07 |
| bone | 0.67 ± 0.05 | 0.17 ± 0.03 | 0.51 ± 0.03 | 0.17 ± 0.03 |

TABLE 5

Comparison of Infected thigh to normal tissue ratios.

| Tissue | ¹¹¹In-IgG* | ¹¹¹In-Streptavidin* | Streptavidin/¹¹¹In-Biotin* | ¹⁸F-biotin 1 |
|---|---|---|---|---|
| normal muscle | 4.5 | 4.4 | 13.0 | 6.1 |
| Blood | 0.3 | 0.8 | 6.2 | 3.1 |
| Liver | 1.1 | 1.2 | 9.3 | 3.5 |
| Kidney | 0.8 | 0.3 | 0.8 | 2.0 |

*As reported in Rusckowski M, Fritz B, Hnatowich D J. Localization of infection using streptavidin and biotin: an alternative to nonspecific polyclonal immunoglobulin. J. Nucl. Med. 33: 1810–1815 (1992).

TABLE 6

Comparison of E. coli infected thigh to normal thigh ratios for various radiopharmaceuticals

| Agents | Infected/normal muscle ratio | Time | Reference |
|---|---|---|---|
| ⁶⁷Ga-citrate | 2.6 ± 0.6 | 4 | *1 |
| ⁹⁹ᵐTc-HSA | 4.1 ± 0.6 | 4 | *1 |
| ¹²⁵I-TNT-1 | 3.3 ± 0.5 | 4 | *1 |
| ⁹⁹ᵐTc-TNT-1 | 3.4 ± 0.08 | 4 | *1 |
| ⁹⁹ᵐTc-IgG | 3.0 ± 1.1 | 4 | *1 |
| ¹¹¹In-IgG | 4.5 | 6 | *2 |
| ¹¹¹In-Streptavidin | 4.4 | 6 | *2 |
| Streptavidin + ¹¹¹In-Biotin | 13 | 3 | *2 |
| ¹¹¹In-Biotin | minimal | 3 | *2 |
| ¹⁸F-Biotin 1 | 6.1 ± 1.1 | | |

TABLE 6-continued

Comparison of E. coli infected thigh to normal thigh ratios for various radiopharmaceuticals

| Agents | Infected/normal muscle ratio | Time | Reference |
|---|---|---|---|

All values are reported for E. coli infection in right thigh. TNT = antinucleus antibody
*1 Hnatowich D J et al., (1992) J. Nucl. Med. 33: 934–935;
*2 Rusckowski, M et al., (1992) J. Nucl. Med. 33: 1810–1815.

EXAMPLE 4

Biotin Compounds for Treating Malaria and Tuberculosis

Antisense oligonucleotides to genes involved in the growth (e.g. aspartate semialdehyde dehydrogenase (asu) or aspartakinase (ask) or cell wall or mycolic acid synthesis of Mycobacterium tuberculosis and Plasmodium falciparum can be conjugated to a biotin compound as described above and administered to a subject to prevent or treat tuberculosis or malaria.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method for directly targetting a therapeutic or imaging agent to a site of infection comprising the steps of:
   a) conjugating the agent, that is not an antibody, to biotin via a non-alkyl linkage, thereby forming a biotin compound that has a high specificity for the site of infection; and
   b) without pre- or post- administering avidin or streptavidin, administering an effective amount of the biotin compound to the subject, so that the biotin compound becomes localized at the site of infection.

2. A method of claim 1, wherein step b), the biotin compound becomes localized at the site of infection within 1 hour after being administered.

3. A method of claim 1, wherein step b), the biotin compound becomes localized at the site of infection at a target to non-target ratio of at least 5:1.

4. A method of claim 1, wherein the agent is a therapeutic agent.

5. A method of claim 4, wherein the therapeutic agent is selected from the group consisting of a drug, toxin, radionuclide, hormone antagonist, heavy metal complex, oligonucleotide, chemotherapeutic nucleotide, peptide, non-specific (non-antibody) protein, boron containing compound and an enediyne.

6. A method of claim 5, wherein the radionuclide is selected from the group consisting of: I-131, Re-186, Re-188, Y-90, Bi-212, At-211, Sr-89, Ho-166, Sm-153, Cu-67 and Cu-64.

7. A method of claim 1, wherein the site of infection is selected from the group consisting of: a bacterial, viral, fungal or protozoal infection.

8. A method of claim 1, wherein the agent is an imaging agent.

9. A method of claim 8, wherein the imaging agent is selected from the group of consisting of: In-111, Tc-99m, I-123, I-125, F-18, Ga-67, Ga-68, a paramagnetic atom and a contrast agent.

10. A method for directly targetting a therapeutic or imaging agent to a tumor comprising the steps of:
   a) conjugating the agent, that is not an antibody, to biotin via a non-alkyl linkage, thereby forming a biotin compound that has a high specificity for the tumor; and
   b) without pre- or post administering avidin or streptavidin, administering an effective amount of the biotin compound to the subject, so that the biotin compound becomes localized at the tumor.

11. A method of claim 10, wherein step b), the biotin compound becomes localized at the site of infection within 1 hour after being administered.

12. A method of claim 10, wherein step b), the biotin compound becomes localized at the site of infection at a target to non-target ratio of at least 5:1.

13. A method of claim 10, wherein the agent is a therapeutic agent.

14. A method of claim 13, wherein the therapeutic agent is selected from the group consisting of a drug, toxin, radionuclide, hormone antagonist, heavy metal complex, oligonucleotide, chemotherapeutic nucleotide, peptide, non-specific (non-antibody) protein, boron containing compound and an enediyne.

15. A method of claim 14, wherein the radionuclide is selected from the group consisting of: I-131, Re-186, Re-188, Y-90, Bi-212, At-211, Sr-89, Ilo-166, Sm-153, Cu-67 and Cu-64.

16. A method of claim 1, wherein the tumor is selected from the group consisting of a minor of the brain, lung, ovary, prostate, breast and colon.

17. A method of claim 1, wherein the agent is an imaging agent.

18. A method of claim 17, herein the imaging agent is selected from the group consisting of: In-111, Tc-99m, I-123, I-125, F-18, Ga-67, Ga-68, a paramagnetic atom and a contrast agent.

19. A method of claim 1, wherein the biotin compound is a biotin amide analog.

20. A method of claim 10, wherein the biotin compound is a biotin amide analog.

21. A method of claim 1, wherein step a), the agent is conjugated to biotin using a crosslinking agent selected from the group consisting of lysine or 6-hydrazinonicotimide (HYNIC).

22. A method of claim 10, wherein step a), the agent is conjugated to biotin using a crosslinking agent selected from the group consisting of lysine or 6-hydrazinonicotimide (HYNIC).

23. A method of claim 1, wherein step b), the biotin compound is administered orally or transdermally.

24. A method of claim 10, wherein step b), the biotin compound is administered orally or transdermally.

* * * * *